United States Patent
Abedin et al.

(10) Patent No.: US 10,896,762 B2
(45) Date of Patent: Jan. 19, 2021

(54) 3D WEB-BASED ANNOTATION

(71) Applicant: INTERNATIONAL BUSINESS MACHINES CORPORATION, Armonk, NY (US)

(72) Inventors: Shafiqul Abedin, San Jose, CA (US); Hakan Bulu, Los Gatos, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/567,553

(22) Filed: Sep. 11, 2019

(65) Prior Publication Data

US 2020/0005945 A1 Jan. 2, 2020

Related U.S. Application Data

(63) Continuation of application No. 15/807,129, filed on Nov. 8, 2017.

(51) Int. Cl.
*G06T 15/00* (2011.01)
*G16H 50/50* (2018.01)
(Continued)

(52) U.S. Cl.
CPC ............. *G16H 50/50* (2018.01); *G06F 3/011* (2013.01); *G06F 3/0346* (2013.01); *G06F 3/04815* (2013.01); *G06F 3/04845* (2013.01); *G16H 30/20* (2018.01); *G16H 30/40* (2018.01); *G16H 40/20* (2018.01); *G06T 2210/41* (2013.01); *G06T 2219/008* (2013.01)

(58) Field of Classification Search
CPC ... G06T 7/0012; G06T 19/00; G06T 2210/41; G06T 2207/30012; G06T 2219/004; G06T 2219/008; G06F 3/04815; G06F 3/04845; G06F 3/011; G06F 3/0346; G16H 50/50; G16H 30/40; G16H 40/20; G16H 30/20
USPC ........................................................ 345/418
See application file for complete search history.

(56) References Cited

U.S. PATENT DOCUMENTS 6,788,969 B2 9/2004 Dupree et al.
7,158,692 B2 1/2007 Chalana et al.
(Continued)

OTHER PUBLICATIONS

A. P. Dhawan and L. Arata, "Knowledge-based 3D analysis from 2D medical images," in IEEE Engineering in Medicine and Biology Magazine, vol. 10, No. 4, pp. 30-37, Dec. 1991.*
(Continued)

*Primary Examiner* — Phu K Nguyen
(74) *Attorney, Agent, or Firm* — Erik Huesits; Stephen Kenny; Foley Hoag, LLP (57) ABSTRACT

Web-based annotation of three dimensional medical imagery is provided. In various embodiments, a plurality of two dimensional medical images is read from a data store. The plurality of two dimensional images is a subset of a three dimensional medical imaging study. The plurality of two dimensional medical images is provided to a remote user. Regional annotations for each of the plurality of medical images are received from the remote user. A volumetric description of the three dimensional imaging study is generated by interpolation of the regional annotations. The volumetric description of the three dimensional imaging is provided for rendering and display to the remote user.

20 Claims, 6 Drawing Sheets

(51) Int. Cl.
*G06F 3/01* (2006.01)
*G06F 3/0346* (2013.01)
*G06F 3/0484* (2013.01)
*G06F 3/0481* (2013.01)
*G16H 30/20* (2018.01)
*G16H 30/40* (2018.01)
*G16H 40/20* (2018.01)

(56) References Cited

U.S. PATENT DOCUMENTS

| | | | |
|---|---|---|---|
| 8,771,189 B2* | 7/2014 | Ionasec | G06T 7/0016 600/437 |
| 8,774,560 B2 | 7/2014 | Sugaya et al. | |
| 8,792,694 B2 | 7/2014 | Batman et al. | |
| 8,879,813 B1 | 11/2014 | Solanki et al. | |
| 8,885,901 B1* | 11/2014 | Solanki | G16H 30/20 382/128 |
| 9,008,391 B1* | 4/2015 | Solanki | G16H 30/20 382/128 |
| 9,147,268 B2 | 9/2015 | Chen et al. | |
| 9,402,601 B1 | 8/2016 | Berger et al. | |
| 9,795,446 B2 | 10/2017 | DiMaio et al. | |
| 9,934,568 B2 | 4/2018 | Reicher et al. | |
| 9,956,054 B2 | 5/2018 | Aguirre-Valencia | |
| 10,121,272 B2 | 11/2018 | Nabatame et al. | |
| 10,275,130 B2 | 4/2019 | De Swarte et al. | |
| 10,416,833 B2 | 9/2019 | Lee et al. | |
| 2007/0279435 A1 | 12/2007 | Ng et al. | |
| 2012/0035963 A1 | 2/2012 | Qian et al. | |
| 2014/0176661 A1 | 6/2014 | Smurro et al. | |
| 2015/0110372 A1* | 4/2015 | Solanki | G16H 30/20 382/130 |
| 2015/0160844 A1 | 6/2015 | Kim et al. | |
| 2016/0349957 A1 | 12/2016 | Lee et al. | |
| 2018/0329609 A1 | 11/2018 | De Swarte et al. | |
| 2019/0042828 A1* | 2/2019 | Solanki | G06T 7/0014 |
| 2019/0205013 A1 | 7/2019 | De Swarte et al. | |

OTHER PUBLICATIONS

Goryawala M, Gulec S, Bhatt R, McGoron AJ, Adjouadi M. A low-interaction automatic 3D liver segmentation method using computed tomography for selective internal radiation therapy. BioMed research international. 2014;2014.*

Moulick et al, Image Compression Using K-Means Clustering and Nuclear Medicine Image Processing, International Journal of Innovative Research in Computer and Communication Engineering, vol. 1, Issue 4, Jun. 2013.*

Norouzi et al, Medical Image Segmentation Methods, Algorithms, and Applications, Faculty of Computing, Universiti Teknologi Malaysia, Johor, Malaysia, Jul. 2014.*

Al-Zu'bi S, Al-Ayyoub M, Jararweh Y, Shehab MA. Enhanced 3d segmentation techniques for reconstructed 3d medical volumes: Robust and accurate intelligent system. Procedia computer science. Jan. 1, 2017;113:531-8.*

Fang L, Li S, Kang X, Izatt JA, Farsiu S. 3-D adaptive sparsity based image compression with applications to optical coherence tomography. IEEE transactions on medical imaging. Jan. 1, 2015;34(6):1306-20.*

Hanbury et al., "Cloud-Based Benchmarking of Medical Image Analysis," SpringerOpen, 1-256 (2017).

Koehl et al., "PACS-based interface for 3D anatomical structure visualization and surgical planning," InMedical Imaging, 4681:17-25 (2002).

Leng et al., "Medical image interpolation based on multi-resolution registration," Computers & Mathematics with Applications, 66(1):1-8 (2013).

Soler et al., "Real-time 3D image reconstruction guidance in liver resection surgery," Hepatobiliary Surgery and Nutrition, 3(2):73 (2014).

Yanhui Liang et al.; A Framework for 3D Vessel Analysis using Whole Slide Images of Liver Tissue Sections; Int J Comput Biol Drug; Jul. 1, 2016; 9(1-2): 102-119. doi:10.1504/IJCBDD.2016.074983.

Yongmei Wang et al.; 3D Image Interpolation Based on Directional Coherence; citeseerx.ist.psu.edu.

* cited by examiner

3D WEB-BASED ANNOTATION

CROSS-REFERENCE TO RELATED APPLICATIONS

This application is a continuation of U.S. patent application Ser. No. 15/807,129, filed on Nov. 8, 2017, which is hereby incorporated by reference in its entirety.

BACKGROUND

Embodiments of the present invention relate to annotation of medical imagery, and more specifically, to 3D web-based annotation.

BRIEF SUMMARY

According to embodiments of the present disclosure, methods of and computer program products for medical imagery annotation are provided. In various embodiments, a plurality of two dimensional medical images is read from a data store. The plurality of two dimensional images is a subset of a three dimensional medical imaging study. The plurality of two dimensional medical images is provided to a remote user. Regional annotations for each of the plurality of medical images are received from the remote user. A volumetric description of the three dimensional imaging study is generated by interpolation of the regional annotations. The volumetric description of the three dimensional imaging is provided for rendering and display to the remote user.

DETAILED DESCRIPTION

Medical image annotation is an important step in the analysis of increasingly large imaging studies. However, annotation of 3-dimensional imagery poses significant challenges, particularly when readers are not necessarily located at the same site as a medical imaging repository. In particular, applying convention al 2-dimensional annotation methods to 3-dimensional imagery is bandwidth intensive and results in the transmission of an excessive number of frames. Volumetric annotation is particularly challenging in this regard.

To address this and other shortcomings of alternative approaches, the present disclosure provides systems and methods for 3-dimensional annotation of medical imagery via a thin client application such as may be provided through a web interface. In some embodiments, a plurality of 2D images are sent to a client. A user performs annotation on those images at the client side. The annotations are then sent back to a server. The server performs volumetric interpolation, and then provides 3D imagery back to the client for display to a user. In various embodiments, rendering is performed on the client side, while the server provides the interpolated slices.

For fast manual segmentation on 3D images, interpolation techniques may be applied such that only a subset of 2D slices are manually segmented and the 3D segmentation is reconstructed. In addition to speed improvement, interpolation-based manual segmentation is advantageous for web-based annotation. Due to its suitability for accommodating collaborating efforts, web-based annotation is popular for large scale annotation tasks. However, transferring 3D medical images can be time consuming, especially through low bandwidth connections such as virtual private network (VPN). With interpolation-base annotation, data transfer delays can be reduced for 3D annotation tasks by only transferring a small portion of the data, that is a pre-selected subset of slices that need to be manually segmented. If image context information is necessary for certain manual segmentation tasks, slices near the selected slices can be transferred as well.

Various interpolation techniques may be applied according to the present disclosure. For example, some embodiments may apply shape-based or morphology-based inter-slice interpolation. Some embodiments may apply image-based deformable registration. However, it will be appreciated that various different interpolation algorithms may be applied according to the anatomical region reflected in a given study.

It will be appreciated that the systems and methods of the present disclosure are applicable to various PACS systems and architectures. A Picture Archiving and Communication System (PACS) is a medical imaging system that provides storage and access to images from multiple modalities. In many healthcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM.

A PACS may handle images from various medical imaging instruments, such as X-ray plain film (PF), ultrasound (US), magnetic resonance (MR), Nuclear Medicine imaging, positron emission tomography (PET), computed tomography (CT), endoscopy (ES), mammograms (MG), digital radiography (DR), computed radiography (CR), Histopathology, or ophthalmology. However, a PACS is not limited to a predetermined list of images, and supports clinical areas beyond conventional sources of imaging such as radiology, cardiology, oncology, or gastroenterology.

Figure 1:
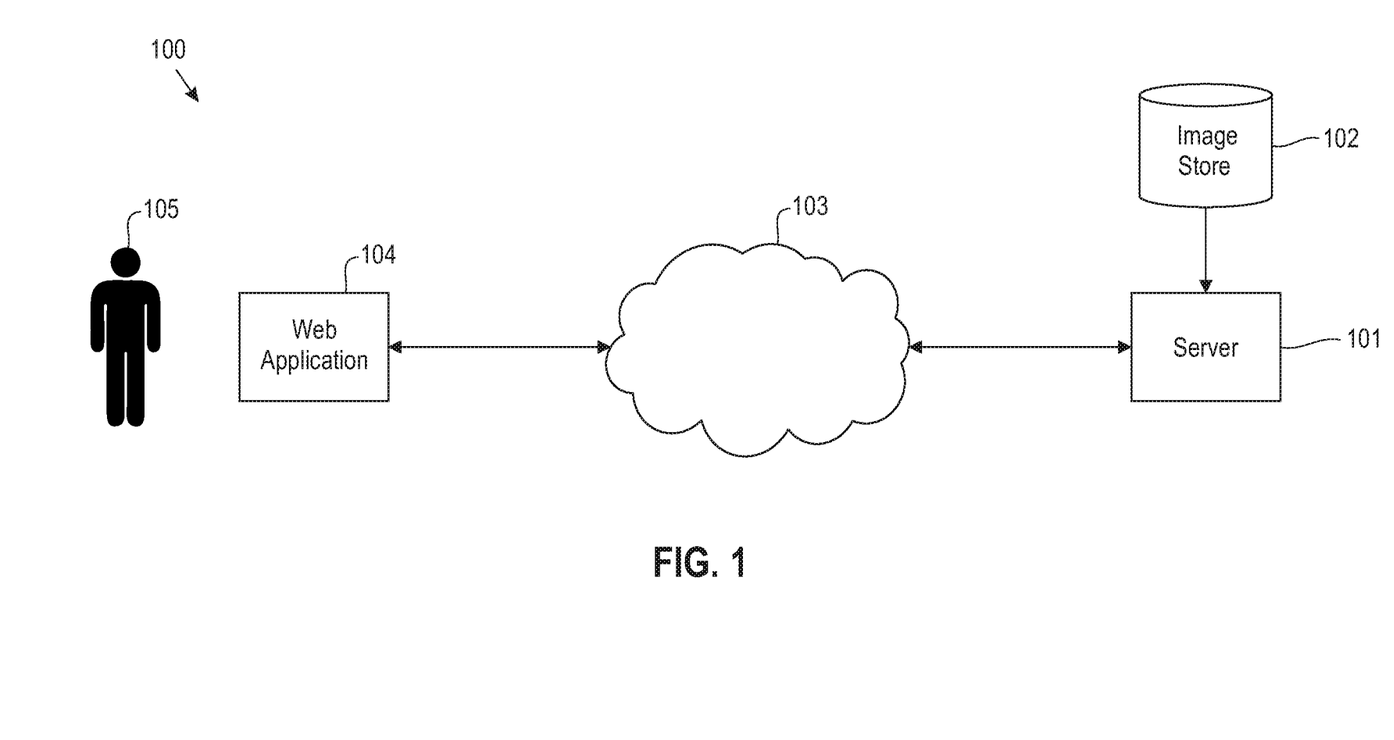
FIG. 1 illustrates a system for medical imagery annotation according to embodiments of the present disclosure.

Referring now to FIG. 1, a system 100 for medical imagery annotation according to embodiments of the present disclosure is illustrated. Server 101 retrieves one or more medical imaging studies from image store 102. In some embodiments, image store 102 may be a PACS. Server 101 provides an interface accessible via network 103 by web application 104. In some embodiments, network 103 is a LAN. In some embodiments, network 103 is the internet. User 105 views medical imagery via web application 104 and performs annotation.

In various embodiments, server 101 retrieves collections of medical imagery for annotation from image store 102. In some embodiments, collections are selected by search or browsing within image store 102. In some embodiments, user 105 has access to search and browse images from image store 102, while in other embodiments an administrator (not pictured) assigns medical imaging studies for annotation to user 105.

In various embodiments, a user may perform image-level annotation via the web interface. In general, an image is displayed, and the user may select the appropriate labels. In this way, a collection may be implicitly created through commonality of labeling.

In various embodiments, a user may perform slide-level annotation via the web interface. In general, the user may create annotations for images in slides via the web interface. The annotations are stored and the image may be added implicitly to collections according to those annotations.

In various embodiments, a user may perform regional annotation via the web interface. In general, a single study is displayed for annotation. An annotation template is displayed as needed for the individual study. In this way, ease-of-use annotation of contours is provided using 3D interpolation across study frames. The annotations are stored as features with studies.

Systems and methods of the present disclosure are suitable for use with a variety of slice selection and interpolation methods, which are generally performed at the server side to identify appropriate slices for dispatch to the user, and then to construct an appropriate. Various suitable methods are described in commonly owned U.S. application Ser. No. 15/357,667, filed Nov. 21, 2016, and Ser. No. 15/389,860, filed Dec. 23, 2016, which are hereby incorporated by reference in their entirety. For example, for fast manual segmentation on 3D images, interpolation techniques may be applied such that only a subset of 2D slices are manually segmented and the 3D segmentation is reconstructed through inter-slice label propagation. In addition to speed improvement, interpolation-based manual segmentation has advantages for web-based annotation. With interpolation-base annotation, data transfer delays can be reduced for 3D annotation tasks by only transferring a small portion of the data, that is a pre-selected subset of slices that need to be manually segmented. If image context information is necessary for certain manual segmentation tasks, slices near the selected slices can be transferred as well.

Given a 3D image with n 2D slices, for fast manual annotation, only a subset of the 2D slices are selected for manual segmentation. The 3D segmentation for the entire volume may be reconstructed by various methods such as interpolation or propagating and fusing labels from manually labeled slices to the remaining unlabeled 2D slices. Uniformly distributed slices may be selected for annotation. However, uniform slice selection may not be optimal for 3D reconstruction, and so alternative slice distributions may be used.

Figure 2:
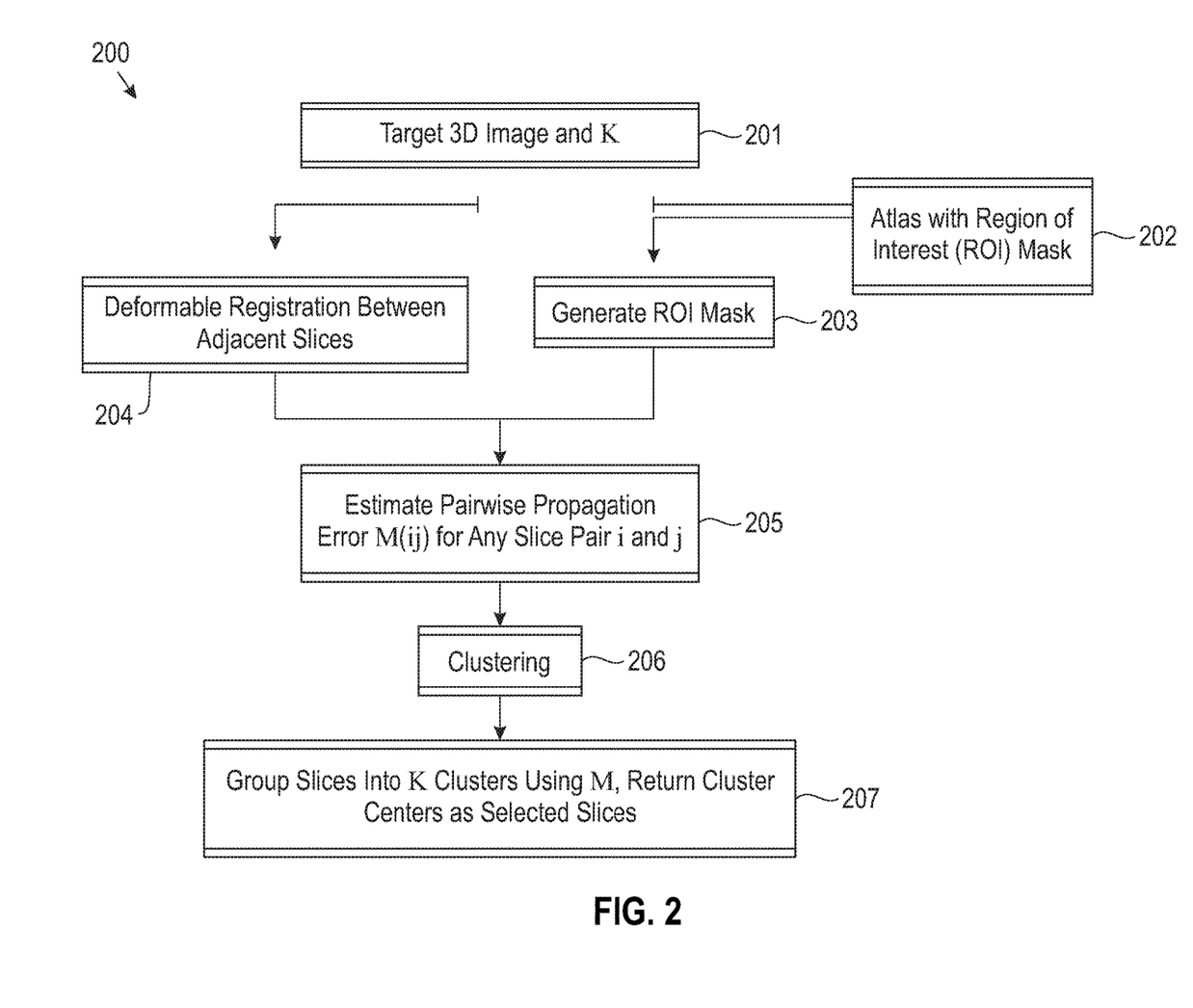
FIG. 2 illustrates an exemplary slice selection method according to embodiments of the present disclosure.

Referring to FIG. 2, an exemplary slice selection method suitable for use according to the present disclosure is illustrated. At 201, a target 3D image comprising a plurality of slices is read. A target number of slices K is also read. At 202, the image is registered against an atlas to generate a region of interest (ROI) mask at 203. At 204, deformable registration is performed between each adjacent slice. In some embodiments, deformable registration between non-adjacent 2D slices is produced by composing registrations produced for adjacent slices located between the two non-adjacent slices. At 205, estimated pairwise propagation error between any two slices i and j is calculated as set forth below. In some embodiments, estimated pairwise propagation error $M(i,j)$ is defined by Equation 4, as set forth below. In some embodiments, the pairwise propagation error is computed only within the ROI mask, thereby disregarding error stemming from features outside of the region of interest. At 206, k-means clustering is applied to cluster the slices in to K clusters based on the estimated pairwise propagation error M. At 207, the slices corresponding to the center of each of the K clusters are returned as the selected slices. The selected slices may then be supplied to an annotator for annotation.

3D segmentation reconstruction accuracy of interpolation methods depends on the overall label propagation accuracy. Accordingly, the slice selection problem is addressed herein by minimizing the overall label propagation errors from selected slices. Inter-slice propagation error is defined according to Equation 1, where $L_i$ is the manual segmentation of slice i and $L_{j \to i}$ is the warped manual segmentation from j to i. x indexes through a 2D slice. $I(\bullet)$ is an indication function.

$$E_{j \to i} = \sum_x I(L_{j \to i}(x) \neq L_i(x)) \quad \text{Equation 1}$$

Let $S = \{s_1, \ldots, s_K\}$ be a set of K selected slices with $s_1 < \ldots < s_K$ and $\bar{S}$ be the set of unselected slices. The overall propagation error using S is given by Equation 2 where $c(S,i) = \text{argmin}_{j \in S} E_{j \to i}$ is the selected slice that produces the least propagation error for slice i. As discussed above, either $c(S,i) = \text{argmax}_{j < i, j \in S}$ or $c(S,i) = \text{argmin}_{i > i, j \in S}$. The selected slices should minimize the overall propagated error, i.e., $S = \text{argmin}_{|S|=K} E(S)$.

$$E(S) = \sum_{i \in \bar{S}} E_{c(S,i) \to i} \quad \text{Equation 2}$$

With the above formulation, slice selection can be solved through clustering, where selected slices are cluster centers and the members of each cluster are slices that the cluster center produces the least propagation error for. Let matrix M stores pairwise propagation error between every slice pair, where $M(j,i) = E_{j \to i}$. Given M, slice selection is solved as set forth below. The clustering algorithm will converge to a local optimal solution from the initialization. To find a more global optimal solution, the clustering algorithm may be repeated multiple times with independently generated random initializations to return the solution giving the minimal overall propagation error. In the below experiments, the number of re-initializations is fixed at 1000.

According to various embodiments, a clustering algorithm for slice selection is provided as follows. For input $M_{n \times n}$ and K<n, cluster centers S are randomly initialized. Clusters are assigned for each slice as follows, for i=1 . . . n, $c(S,i) = \text{argmin}_{j \in S} E_{j \to i}$. For each cluster, the members are calculated and the cluster center is updated as follows, for k=1 . . . K, $C_k = \{j | c(S,j) = s_k\}$ and then $s_k = \text{argmin}_{i \in C_k} \Sigma_{j \in C_k} M(i,j)$. If no changes result from the above, or the maximal number of iterations is reached, S is returned. Otherwise, the process is repeated from cluster assignment.

Inter-slice label propagation error is estimated from image intensity differences according to Equation 3, where $F_i$ is the image for slice i and $F_{j \to i}$ is the warped image from slice j to slice i. $\alpha$ is a model parameter. The model captures the relations between segmentation label and image intensity, which is application dependent. The model parameter is mainly determined by three factors: 1) inter-slice registration accuracy, 2) noise levels in image acquisition and 3) how distinguishable different anatomical structures are based on intensity information. When inter-slice registration is accurate, noise level is low and anatomical structures can be well distinguished by intensity information, large α tends to fit the model better. Otherwise, small α may be more suitable.

$$p(L_{j \to i}(x) \neq L_i(x)) \propto |F_{j \to i}(x) - F_i(x)|^\alpha \quad \text{Equation 3}$$

Using the intensity-based label propagation error model, M(j,i) is given by Equation 4.

$$M(j, i) = \begin{cases} \sum_{x \in ROI} |F_{j \to i}(x) - F_i(x)|^\alpha & |i - j| \leq D \\ \infty & |i - j| > D \end{cases} \quad \text{Equation 4}$$

In general, registration is capable of reducing anatomical variations between nearby slices. For slices that are too far away, the anatomy content may be too different to be compensated by registration. Hence, label propagation is only considered between nearby slices, as specified by D. The ROI is a mask covering the region of interest for segmentation. To generate the ROI, a template is built from a set of testing images. The ROI mask can be manually labeled in the template.

Figure 3:
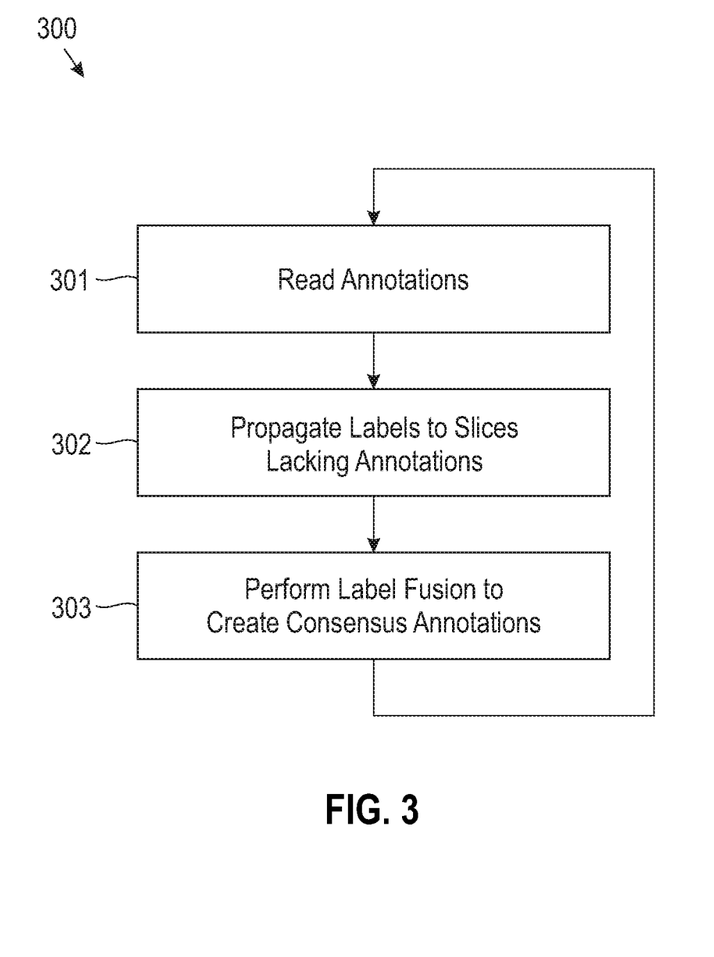
FIG. 3 illustrates an exemplary slice interpolation method according to embodiments of the present disclosure.

Referring to FIG. 3, an exemplary method for 3D segment reconstruction according to embodiments of the present disclosure is illustrated. An image study comprises a plurality of 2D slices that together describe a 3D volume. At 301, annotations are read for a subset of the 2D slices. The annotations include anatomical labeling of at least one anatomical feature. These annotations may be manual, or may be the result of various automatic annotation processes. For a 2D slice lacking annotations, at 302, anatomical labels are propagated to it from at least one neighbor. In some embodiments, neighboring slices from either side of the slice are used. Where labels are prorogated form multiple slices, joint label fusion is applied at 303 to fuse the two propagated annotations into a consensus annotation. The process may be repeated, iterating over all slices lacking annotations. Anatomical labels are propagated between any two slices through calculating deformable image registration between the two slices. In some embodiments, deformable registration between adjacent 2D slices is calculated using ANTs registration. In other embodiments, deformable registration is calculated by optical flow. In some embodiments, deformable registration between non-adjacent 2D slices is produced by composing registrations produced for adjacent slices located between the two non-adjacent slices. Accordingly, fewer manually segmented slices are required for accurate 3D reconstruction than in alternative interpolation schemes.

According to various embodiments, registration-based interpolation is applied for inter-slice label propagation. To this end, deformable registration is computed between adjacent slices. Deformable registration between non-adjacent slices is calculated by composing deformation fields of adjacent slices located between them. Let $\phi_{i \to i+1}$ be the diffeomorphic map from slice i to slice i+1. Then, $\phi_{i \to j} = \phi_{i \to i+1} \circ \ldots \circ \phi_{j-1 \to j}$ for any j>i. Comparing to directly estimating pairwise registration between any slice pairs, the composition-based approach is more efficient because O(n) registrations are needed as opposed to O(n²). Furthermore, deformation composition avoids more difficult problems of estimating large deformations between far apart slices.

Since the anatomical similarity between two slices usually decreases as the inter-slice distance increases, it is expected that label propagation error also increases as inter-slice distance increases. Hence, given a set of manually segmented slices S, for an unlabeled slice i, at most two annotated slices from S, i.e., $\text{argmax}_{j < i, j \in S}$ and $\text{argmin}_{i > i, j \in S}$, will be applied to segment slice i.

For slices that have labels propagated from two manually labeled slices, a patch-based label fusion approach is applied to fuse the labels. For each patch of size 7×7 in a target slice, the two corresponding patches from the warped slices are fused by locally weighted voting, where the voting weights are computed by using the joint label fusion algorithm.

Various deformable registration methods are suitable for according to the present disclosure. For example, image-based registration may be computed using the Advanced Normalization Tools (ANTs) software. Such registration sequentially optimizes an affine transform and a deformable transform (Syn) between a pair of images, using the Mattes mutual information metric. In a multi-atlas case, image similarity based local weighted voting may be applied for combining the candidate segmentations produced by different atlases for the same target image. The voting weights may be computed using the joint label fusion technique. Joint label fusion as provided by ANTs may be applied.

In other embodiments, optical flow based registration is applied instead. In general, optical flow based registration requires a larger number of manually annotated slices, but is faster than the above outlined methods. In optical flow based approaches, a vector field is computed indicating the movement of a pixel from image to image. In sparse approaches, the vector field is limited to pixels of interest, as extracted in a preprocessing step by, e.g., Shi-Tomashi or Harris algorithms. Based on the vector field, intermediate labels may be computed.

Figure 4:
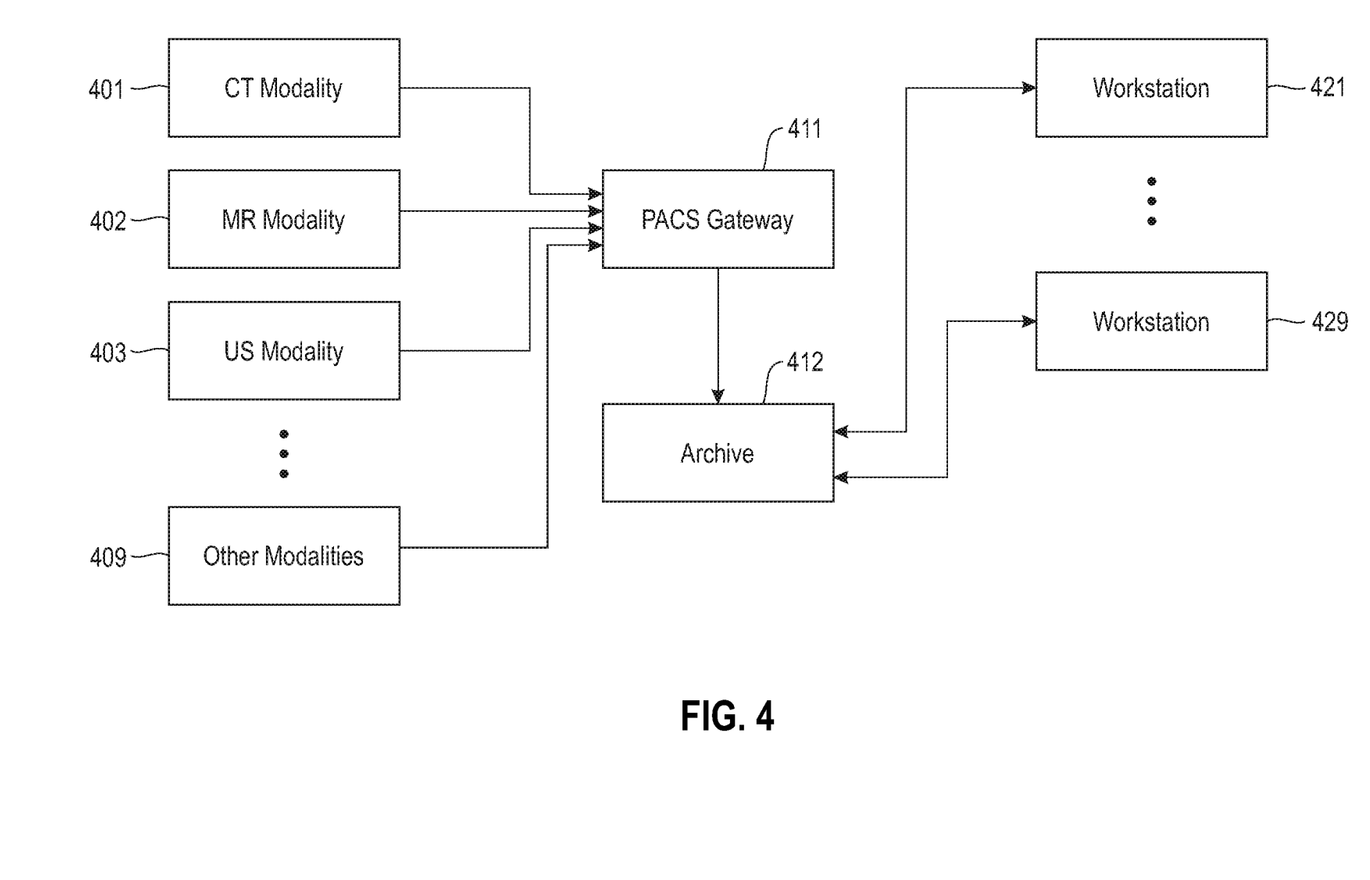
FIG. 4 depicts an exemplary Picture Archiving and Communication System.

Referring to FIG. 4, an exemplary PACS 400 consists of four major components. Various imaging modalities 401 . . . 409 such as computed tomography (CT) 401, magnetic resonance imaging (MM) 402, or ultrasound (US) 403 provide imagery to the system. In some implementations, imagery is transmitted to a PACS Gateway 411, before being stored in archive 412. Archive 412 provides for the storage and retrieval of images and reports. Workstations 421 . . . 429 provide for interpreting and reviewing images in archive 412. In some embodiments, a secured network is used for the transmission of patient information between the components of the system. In some embodiments, workstations 421 . . . 429 may be web-based viewers. PACS delivers timely and efficient access to images, interpretations, and related data, eliminating the drawbacks of traditional film-based image retrieval, distribution, and display.

A PACS may handle images from various medical imaging instruments, such as X-ray plain film (PF), ultrasound (US), magnetic resonance (MR), Nuclear Medicine imaging, positron emission tomography (PET), computed tomography (CT), endoscopy (ES), mammograms (MG), digital radiography (DR), computed radiography (CR), Histopathology, or ophthalmology. However, a PACS is not limited to a predetermined list of images, and supports clinical areas beyond conventional sources of imaging such as radiology, cardiology, oncology, or gastroenterology.

Different users may have a different view into the overall PACS system. For example, while a radiologist may typically access a viewing station, a technologist may typically access a QA workstation.

In some implementations, the PACS Gateway 411 comprises a quality assurance (QA) workstation. The QA workstation provides a checkpoint to make sure patient demographics are correct as well as other important attributes of a study. If the study information is correct the images are passed to the archive 412 for storage. The central storage device, archive 412, stores images and in some implementations, reports, measurements and other information that resides with the images.

Once images are stored to archive 412, they may be accessed from reading workstations 421 . . . 429. The reading workstation is where a radiologist reviews the patient's study and formulates their diagnosis. In some implementations, a reporting package is tied to the reading workstation to assist the radiologist with dictating a final report. A variety of reporting systems may be integrated with the PACS, including those that rely upon traditional dictation. In some implementations, CD or DVD authoring software is included in workstations 421 . . . 429 to burn patient studies for distribution to patients or referring physicians.

In some implementations, a PACS includes web-based interfaces for workstations 421 . . . 429. Such web interfaces may be accessed via the internet or a Wide Area Network (WAN). In some implementations, connection security is provided by a VPN (Virtual Private Network) or SSL (Secure Sockets Layer). The clients side software may comprise ActiveX, JavaScript, or a Java Applet. PACS clients may also be full applications which utilize the full resources of the computer they are executing on outside of the web environment.

Communication within PACS is generally provided via Digital Imaging and Communications in Medicine (DICOM). DICOM provides a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format.

DICOM groups information into data sets. For example, a file containing a particular image, generally contains a patient ID within the file, so that the image can never be separated from this information by mistake. A DICOM data object consists of a number of attributes, including items such as name and patient ID, as well as a special attribute containing the image pixel data. Thus, the main object has no header as such, but instead comprises a list of attributes, including the pixel data. A DICOM object containing pixel data may correspond to a single image, or may contain multiple frames, allowing storage of cine loops or other multi-frame data. DICOM supports three- or four-dimensional data encapsulated in a single DICOM object. Pixel data may be compressed using a variety of standards, including JPEG, Lossless JPEG, JPEG 2000, and Run-length encoding (RLE). LZW (zip) compression may be used for the whole data set or just the pixel data.

Figure 5:
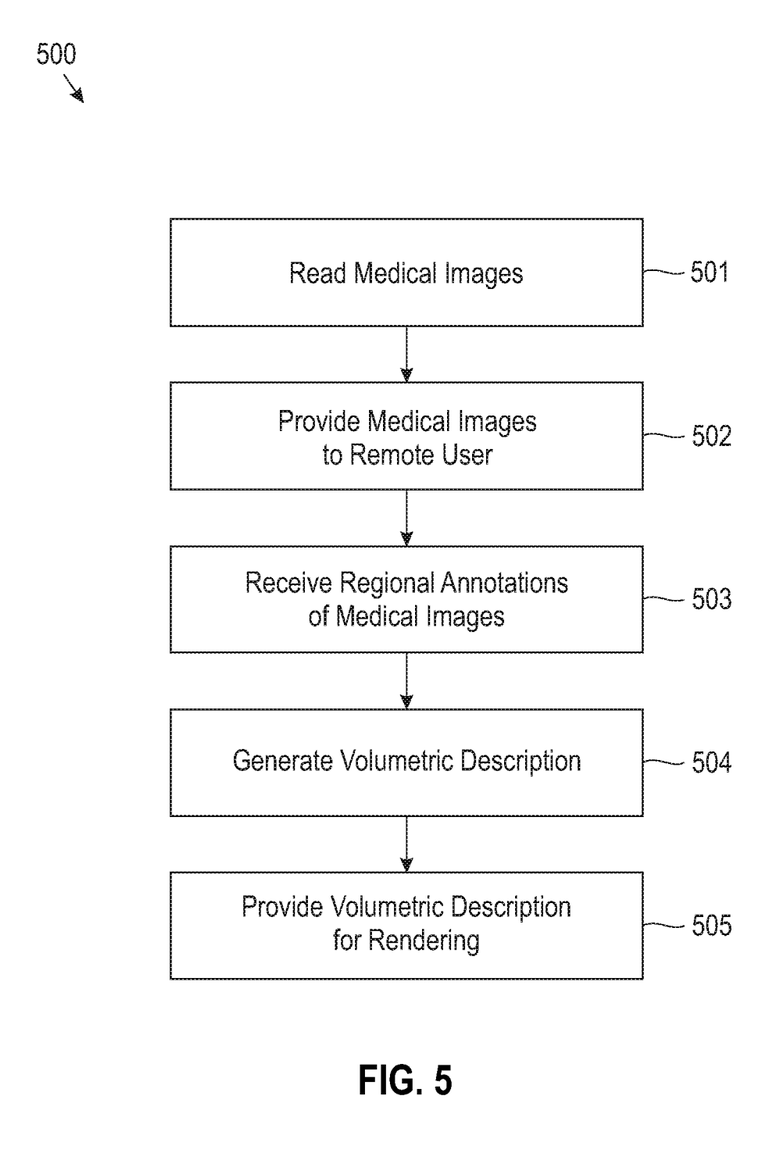
FIG. 5 illustrates a method for medical imagery annotation according to embodiments of the present disclosure.

Referring now to FIG. 5, a method for medical imagery annotation according to embodiments of the present disclosure is illustrated. At 501, a plurality of two dimensional medical images is read from a data store. The plurality of two dimensional images is a subset of a three dimensional medical imaging study. At 502, the plurality of two dimensional medical images is provided to a remote user. At 503, regional annotations for each of the plurality of medical images are received from the remote user. At 504, a volumetric description of the three dimensional imaging study is generated by interpolation of the regional annotations. At 205, the volumetric description of the three dimensional imaging is provided for rendering and display to the remote user.

Figure 6:
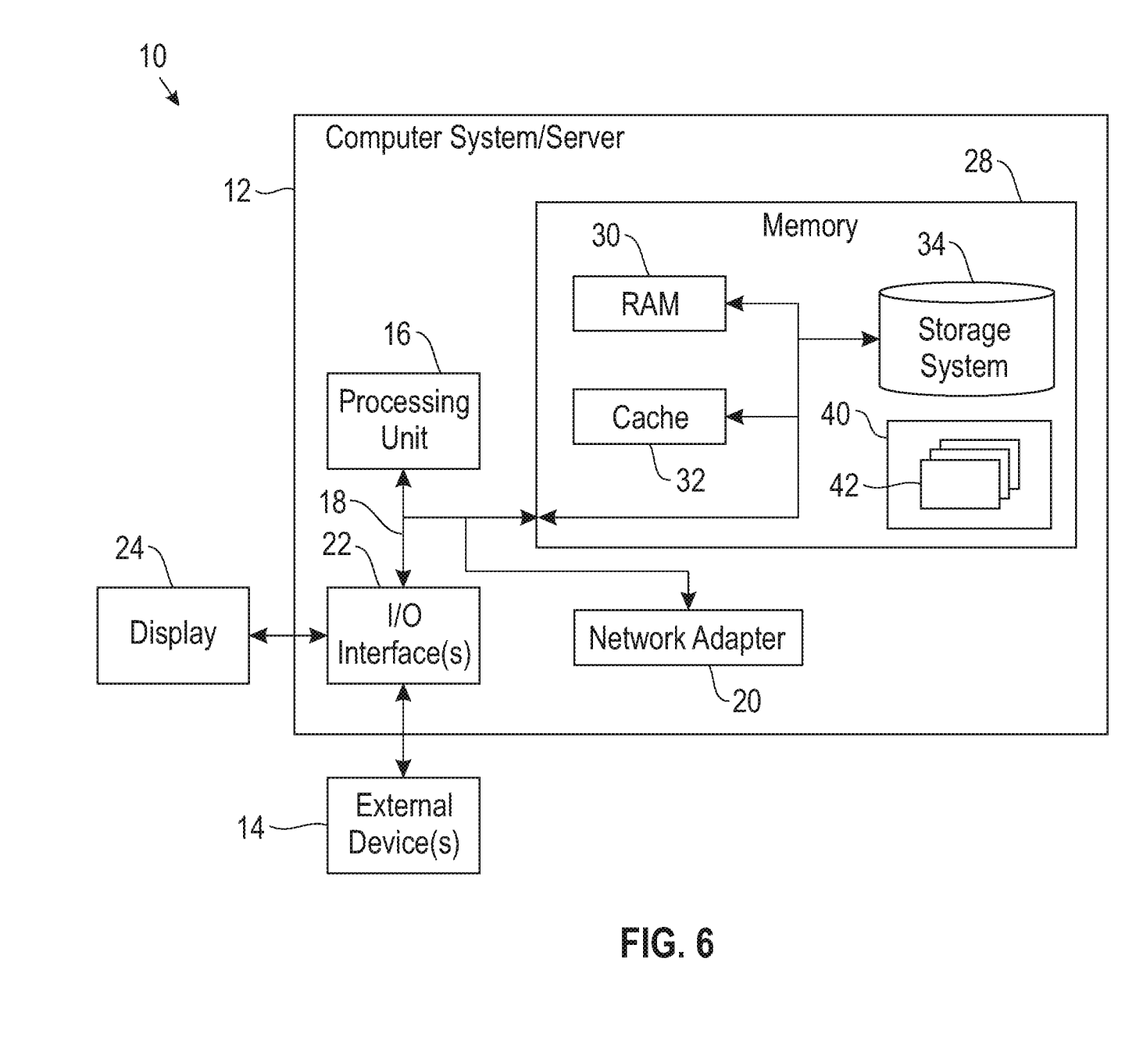
FIG. 6 depicts a computing node according to an embodiment of the present invention.

Referring now to FIG. 6, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 6, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
    reading a three dimensional medical imaging study from a data store, the three dimensional medical imaging study comprising a first plurality of two dimensional medical images;
    selecting a second plurality of two dimensional medical images from the first plurality of two dimensional medical images, the second plurality of two dimensional medical images being a strict subset of the first plurality of two dimensional medical images;
    providing the second plurality of two dimensional medical images to a remote user;
    receiving from the remote user regional annotations for each of the second plurality of medical images;
    generating a volumetric description of the three dimensional imaging study by interpolation of the regional annotations;
    providing the volumetric description of the three dimensional imaging for rendering and display to the remote user, wherein:
        said selecting of the second plurality of two dimensional images minimizes an estimated error rate of the interpolation by selecting the second plurality of two dimensional images to represent clusters of the first plurality of two dimensional images, each cluster having a similar interslice propagation error, and
        the estimated error rate is based on differences in intensity between a plurality of pairs of two dimensional images of the first plurality of two dimensional images.

2. The method of claim 1, wherein the data store comprises a PACS.

3. The method of claim 1, wherein selecting the second plurality of two dimensional medical images comprises applying k-means clustering to the first plurality of two dimensional medical images.

4. The method of claim 3, wherein applying k-means clustering comprises clustering the first plurality of two dimensional medical images based on a minimization of the error rate.

5. The method of claim 3, wherein applying k-means clustering comprises iteratively initializing centers of a plurality of clusters of the first plurality of two dimensional medical images and selecting a clustering having a minimum error rate.

6. The method of claim 1, wherein the second plurality of two dimensional medical images corresponds to centers of clusters obtained by applying k-means clustering to the first plurality of two dimensional medical images.

7. The method of claim 1, wherein the estimated error rate corresponds to a matching between manually segmented images and warped manually segmented images.

8. The method of claim 1, wherein the error rate is based on a predetermined region of the first plurality of two dimensional images.

9. The method of claim 1, further comprising:
    providing a web application to the remote user, the web application being adapted to receive input of the regional annotations from the remote user.

10. The method of claim 1, wherein the second plurality of two dimensional medical images is provided to the remote user via the internet.

11. The method of claim 1, further comprising:
    providing a web application to the remote user, the web application being adapted to render the volumetric description and display the rendering to the remote user.

12. A system comprising:
    a data store;
    a computing node comprising a computer readable storage medium having program instructions embodied therewith, the program instructions executable by a processor of the computing node to cause the processor to perform a method comprising:
        reading a three dimensional medical imaging study from the data store, the three dimensional medical imaging study comprising a first plurality of two dimensional medical images;
        selecting a second plurality of two dimensional medical images from the first plurality of two dimensional medical images, the second plurality of two dimensional medical images being a strict subset of the first plurality of two dimensional medical images;

providing the second plurality of two dimensional medical images to a remote user;

receiving from the remote user regional annotations for each of the second plurality of medical images;

generating a volumetric description of the three dimensional imaging study by interpolation of the regional annotations;

providing the volumetric description of the three dimensional imaging for rendering and display to the remote user, wherein said selecting of the second plurality of images minimizes an estimated error rate of the interpolation by selecting the second plurality of two dimensional images to represent clusters of the first plurality of two dimensional images, each cluster having a similar interslice propagation error, and the estimated error rate is based on differences in intensity between a plurality of pairs of two dimensional images of the first plurality of two dimensional images.

13. The system of claim 12, wherein selecting the second plurality of two dimensional medical images comprises applying k-means clustering to the first plurality of two dimensional medical images.

14. The system of claim 13, wherein applying k-means clustering comprises clustering the first plurality of two dimensional medical images based on a minimization of the error rate.

15. The system of claim 13, wherein applying k-means clustering comprises iteratively initializing centers of a plurality of clusters of the first plurality of two dimensional medical images and selecting a clustering having a minimum error rate.

16. The system of claim 12, wherein the second plurality of two dimensional medical images corresponds to centers of clusters obtained by applying k-means clustering to the first plurality of two dimensional medical images.

17. The system of claim 12, wherein the estimated error rate corresponds to a matching between manually segmented images and warped manually segmented images.

18. The system of claim 12, wherein the error rate is based on a predetermined region of the first plurality of two dimensional images.

19. A computer program product for medical imagery annotation, the computer program product comprising a computer readable storage medium having program instructions embodied therewith, the program instructions executable by a processor to cause the processor to perform a method comprising:

reading a three dimensional medical imaging study from a data store, the three dimensional medical imaging study comprising a first plurality of two dimensional medical images;

selecting a second plurality of two dimensional medical images from the first plurality of two dimensional medical images, the second plurality of two dimensional medical images being a strict subset of the first plurality of two dimensional medical images;

providing the second plurality of two dimensional medical images to a remote user;

receiving from the remote user regional annotations for each of the second plurality of medical images;

generating a volumetric description of the three dimensional imaging study by interpolation of the regional annotations;

providing the volumetric description of the three dimensional imaging for rendering and display to the remote user, wherein said selecting of the second plurality of images minimizes an estimated error rate of the interpolation by selecting the second plurality of two dimensional images to represent clusters of the first plurality of two dimensional images, each cluster having a similar interslice propagation error, and the estimated error rate is based on differences in intensity between a plurality of pairs of two dimensional images of the first plurality of two dimensional images.

20. The computer program product of claim 19, wherein selecting the second plurality of two dimensional medical images comprises applying k-means clustering to the first plurality of two dimensional medical images.

* * * * *